(12) United States Patent
Marahiel et al.

(10) Patent No.: US 8,063,181 B2
(45) Date of Patent: Nov. 22, 2011

(54) METHOD FOR THE PRODUCTION OF CYCLIC MOLECULES

(75) Inventors: Mohamed A. Marahiel, Marburg (DE); Stephan Sieber, Marburg (DE)

(73) Assignee: ZYRUS Beteiligungsgesellschaft mbH & Co. Patent I KG, Schoenfeld, OT Waltersdorf (DE)

( * ) Notice: Subject to any disclaimer, the term of this patent is extended or adjusted under 35 U.S.C. 154(b) by 1071 days.

(21) Appl. No.: 10/566,432

(22) PCT Filed: Jul. 30, 2004

(86) PCT No.: PCT/DE2004/001704
§ 371 (c)(1),
(2), (4) Date: Sep. 19, 2006

(87) PCT Pub. No.: WO2005/012541
PCT Pub. Date: Feb. 10, 2005

(65) Prior Publication Data
US 2007/0184516 A1     Aug. 9, 2007

(30) Foreign Application Priority Data
Jul. 31, 2003  (DE) .................................. 103 35 584

(51) Int. Cl.
*C07K 1/00*  (2006.01)
(52) U.S. Cl. ..................... 530/333; 530/317; 435/68.1
(58) Field of Classification Search .......... 530/333, 530/317; 435/68.1
See application file for complete search history.

(56) References Cited

U.S. PATENT DOCUMENTS
2002/0192773 A1    12/2002  Walsh et al.

FOREIGN PATENT DOCUMENTS
| WO | WO 96/34878 | 11/1996 |
| WO | WO 98/28434 | 7/1998 |
| WO | WO 01/05815 A1 | 1/2001 |
| WO | WO 02/085401 A1 | 10/2002 |

OTHER PUBLICATIONS

Sieber, SA et al. Peptidyl thiophenols as substrates for nonribosomal peptide cyclases. Angew. Chem. 2004. 43:493-498. Published online Jan. 14, 2004.*

J. Grunewald et al., "Chemo- and Regioselective Peptide Cyclization Triggered by the N-Terminal Fatty Acid Chain Length: The Recombinant Cyclase of the Calcium-Dependent Antibiotic from *Streptomyces coelicolor*"; *Biochemistry* 2004, 43, 2915-2925.

R. Kohli et al., "Generality of Peptide Cyclization Catalyzed by Isolated Thioesterase Domains of Nonribosomal Peptide Synthetases", *Biochemistry* 2001, 40, 7099-7108.

T. Keating et al., "Chain Termination Steps in Nonribosomal Peptide Synthetase Assembly Lines: Directed Acyl-S-Enzyme Breakdown in Antibiotic and Siderophore Biosynthesis", *Chembiochem* 2001, 2, 99-107.

C. Tseng et al., "Characterization of the Surfactin Synthetase C-Terminal Thioesterase Domain as a Cyclic Depsipeptide Synthase", *Biochemistry* 2002, 47, 13350-13359.

* cited by examiner

*Primary Examiner* — Allison M. Ford
*Assistant Examiner* — Susan E Fernandez
(74) *Attorney, Agent, or Firm* — Clark & Brody

(57) ABSTRACT

The invention at hand describes a method for the cyclization of peptides and proteins in which linear thioesters serve as substrates. The cyclization is catalyzed by thioesterase domains of NRPS or PKS cyclases. The substrates according to the present invention are composed of one linear peptide on which a charge-stabilized aromatic, heteroaromatic or araliphatic leaving group is bound. These substrates lead to higher yields and reaction rates than linear peptides able to be cyclized with methods known so far and, furthermore, allow the cyclization of such peptides which were previously not able to be cyclized.

15 Claims, 3 Drawing Sheets

METHOD FOR THE PRODUCTION OF CYCLIC MOLECULES

Figure 1:
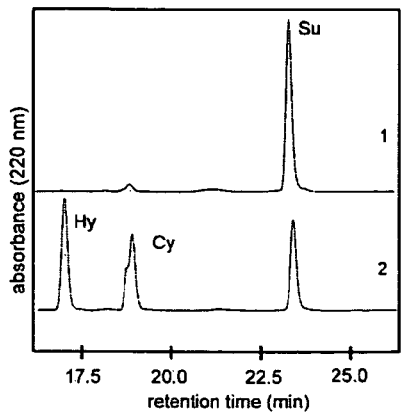

In the search for new pharmaceuticals, natural products are increasingly the focus of science and serve the latter as a lead structure for the development of new agents. Bacteria or fungi synthesize these pharmacologically relevant molecules, and their spectrum of activity extends from

- antibiotic (infectious diseases) to
- cytostatic (cancer) up to
- immunosuppressive (organ transplantation) characteristics.

Within nature, the synthesis of these small molecules mostly occurs in large multienzymes which primarily produce peptides, polyketides or a hybrid of both.

Prominent examples for such compounds are penicillin, cephalosporin, daptomycin, epothilone, cyclosporine, a part of which has been successfully used in medicine for a long time. A common characteristic of these compounds is the cyclic structure which is decisive for the biological activity. Many of the aforementioned compounds feature no or considerably reduced effectivity if they are present in linear form. In contrast to linear molecules, cyclic molecules have reduced conformation flexibility (free movement and rotation) due to the ring formation, what allows only the biologically active form to appear. In this context, nature has selected an interesting strategy which ensures that the synthesized molecule exists in only one modification and thus interacts specifically with only one "target" (attack destination) within the biological system. Targets are most frequently essential parts or functions of a cell, which are important for its survival, such as e.g. the cell wall or protein synthesis. As these molecules selectively eliminate bacterial, fungal or carcinogenic (cancer) cells or viruses while simultaneously protecting the body's own cell tissue, they are of enormous importance for the therapy of infectious diseases and cancer. In addition to that, they can also suppress the immune defense, which effectively inhibits organ rejection with transplantations (cyclosporine).

Due to the intensive application in medicine many of these compounds have unfortunately lost their effectivity, as the systems to be fought have developed resistance mechanisms. Furthermore, many potent agents possess very strong side effects, due to which their medical application is limited (e.g. nephrotoxicity of bacitracin). Hence, a big demand exists for new or optimized chemotherapeutics (antibiotics, cytostatics, immunosuppressants), which should feature as few side effects as possible and interact in a highly specific manner.

For the identification of such new agents, the potent cyclic natural products which are already known can serve as a lead structure and be systematically modified and tested for improved effectivity.

Such natural products are produced in the biological system by non-ribosomal peptide synthetases (NRPS) and cyclized by so called thioesterases/cyclases, which can be recombinantly overproduced with a good yield. These enzymes can reliably and efficiently transfer linear peptides of a given lead structure into cyclic molecules. In natural systems, the activation of the C-terminus (i.e. of the free carboxylic acid of the linear peptide) by a thioester leaving group—the cofactor phosphopantetheine—is the driving force of the cyclization reaction. In the artificial system, the recombinant cyclase reacts with an abridged thioester-mimic of this natural cofactor (N-acetylcysteamie, SNAC). Thioester-mimics are understood to be substances which imitate the function of the natural cofactor, however, are not of a natural origin, possess a thio leaving group and whose aliphatic chain is shorter than those of the natural cofactor phosphopantetheine.

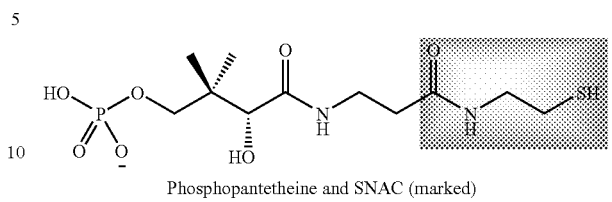

Phosphopantetheine and SNAC (marked)

Tyrocidine cyclase and surfactin cyclase have been characterized so far with the help of the SNAC leaving group. Many other biologically relevant cyclic compounds, such as e.g. fengycin, mycosubtilin, syringomycin and bacitracin do not show any cyclization activity with the respective enzyme on using the SNAC leaving group, which can be explained by an incorrect folding of the enzyme. Other compounds, such as e.g. CDA (calcium dependent antibiotic) and bacillibactine show in part a very bad conversion with the known substrate analoga.

Object of the present invention are non-natural, synthetic cofactors whose chemical qualities as leaving groups ensure an efficient enzyme acylation.

In contrast to the widely held belief among those skilled in the art, no "recognition" of the natural cofactor pantetheine by the enzyme takes place, thus the chemical transfer potential of the acyl residue to the active center within the enzyme is exclusively the decisive factor. The belief prevalent among those skilled in the art that the "recognition" of the natural cofactor pantetheine by the enzyme is the decisive factor for the cyclisation reaction, is presented in, for example, J W Trauger, R M Kohli, H D Mootz, M A Marahiel and C T Walsh, *Nature* 2000, 407: 215-218; R Aggarwal, P Caffrey, P F Leadly, C J Smith and J Staunton, *Journal of the Chemical Society Communications* 1995, 15: 1519-1520 sowie R S Gokhale, D Hunziker, D E Cane and C Khosla, *Chemical Biology* 1999, 6: 117-125.

In contrast to the established SNAC substrates, thiophenol, e.g., features, as a charge-stabilized leaving group according to the present invention, no structural analogy at all to the natural cofactor, provides, however, a significantly better leaving group quality, as the thiol is in conjugation with an aromatic benzene ring. Within other leaving groups according to the present invention the thiol function or the hydroxy function is bound to an $sp^3$ C atom, which is directly bound to the aromatic ring (α-C atom), in such a way that the aromatic system has an inductive effect on the thio groups or the hydroxy groups. Such leaving groups according to the present invention are referred to in the following as araliphatic thio leaving groups or araliphatic hydroxy leaving groups. The expert skilled in the art knows that the inductive effect of an aromatic system has a stabilizing effect on the groups bound to an (α-C-Atom, thus, increasing their leaving group quality. This can be read about e.g. in Michael B. Smith & Jerry March: *March's Advanced Organic Chemistry. Reactions, Mechanisms, and Structure.* 5th Edition 2000, John Wiley & Sons Inc., New York/Chichester/Brisbane/Toronto/Singapore. In the case of the SNAC, neither a conjugation with an aromatic or heteroaromatic system nor stabilization by the inductive effect of an aromatic system in an α-position to the carbon atom, to which the thio group is bound, is available, thus, many enzymes do not show any activity with these substrates or feature low $k_{cat}/K_M$ values.

DESCRIPTION AND STATE OF THE ART

Many valuable pharmaceuticals feature cyclic structures, wherein the rings of these cyclic structures are composed of 5 or more atoms. Methods of synthetic chemistry for manufacturing cyclic compounds known in the state of the art feature numerous disadvantages. These disadvantages include, for example, but not exclusively, low yields of the cyclic products, the necessity of protective groups to block or to protect reactive functional groups, as well as the need to carry out these reactions in organic solvents. These synthetic problems can be overcome by enzymatic methods. EP 0 832 096 B1 describes a method in which a non-oxidized N-terminal cysteine of a first oligopeptide is reacted with the C-terminal thioester of a second oligopeptide. The reaction is catalyzed by a thiol, wherein the thio group is bound directly to an aromatic or heteroaromatic ring. In this, a β-amino thioester is formed as an intermediate, followed by spontaneous intramolecular rearrangement, wherein the amide bond of the oligopeptide is formed. Disadvantages of this method are that the first oligopeptide must possess an N-terminal cysteine and that it is not able to undergo cyclization reactions.

U.S. Pat. No. 6,307,018 B1, in contrast, describes a general method of binding a first C-terminal α-thioester peptide with a second N-terminal amino acid peptide segment, in which the N-terminal amino acid peptide segment does not need to possess an N-terminal cysteine. The second oligopeptide, however, must possess a secondary amino group, which is bound by the N atom of this secondary amino group to a non-oxidized sulfhydryl group of an aromatic thiol. The aromatic thiol can be either a thiophenol, benzylmercaptane, or an S-alkyl benzylmercaptane. Another disadvantage of U.S. Pat. No. 6,307,018 B1 is that either the C-terminus of the first or the N-terminus of the second oligopeptide must be glycine. The method is not suitable for the cyclization of peptides. US 2002/0192773 A1 describes a method for the enzymatic production of macrocyclic molecules, in which recombinant thioesterase domains (TE domains, cyclases) derived from a PKS or NRPS multidomain system are reacted with a substrate, wherein the substrate contains an acyl residue which is activated by a thioester leaving group (and) an adjacent nucleophile. The activated acyl residue and nucleophile are separated from one another by a linear backbone. Hereby, a disadvantage is that the leaving group is not charge-stabilized.

Due to insufficient cyclization activity of many enzymes on using leaving groups which are structurally analogous to the natural cofactor, such as, for example, coenzyme A, phosphopantetheine and N-acetylcysteamine TE-domains are considerably limited in their application. The present invention overcomes this limitation by the use of novel leaving groups and now enables the development of diverse libraries of cyclic bioactive agents of many pharmacologically significant molecule classes.

Surprisingly, and in contradiction with the technical state of the art, it was found that the recognition of the substrates by the enzymes plays no role whatsoever in the cyclization of peptides and proteins and that charge-stabilized thio and hydroxy compounds represent suitable leaving groups for the acylation reaction of peptide cyclases. Charge-stabilized thio- and hydroxy compounds are thereby understood to be aromatic or heteroaromatic ring systems, wherein a hydroxy or thio group is bound to one of the ring atoms or to a carbon atom which is bound to the ring system.

The invention at hand provides substrates with whose help enzymatic cyclization of such peptides and proteins which were not accessible to cyclization according to the state of the art is possible. Moreover, the yield of proteins and peptides, which can be cyclized with methods available according to the state of the art, can be increased with the help of the substrates according to the present invention. Furthermore, the invention at hand provides a method to chemically modify further substrates engaged in the cyclization of peptides and proteins and thereby makes them more easily accessible for cyclization.

AIM OF THE INVENTION

It is the aim of the present invention to improve the method for the production of cyclic peptides by/through the reaction of linear peptides with peptide cyclases, wherein "improvement" means an increased yield of the cyclic peptide and/or acceleration of the cyclization reaction and/or cyclization of peptides which can not be cyclized with methods used thus far. This aim is achieved, according to the present invention, by a method for the production of cyclic peptides, in which a peptide cyclase is brought into contact with a linear peptide, the linear peptide contains an acyl residue which is activated by a nucleophilic leaving group chemically bound to said acyl residue, and the activated acyl residue of the linear peptide selectively acylates the center of the peptide cyclase, wherein the nucleophilic leaving group is cleaved off by the formation of the cyclic peptide and cyclic peptides with rings consisting of at least 5 atoms are formed, wherein the nucleophilic leaving group, which is chemically bound to the acyl residue of the linear peptide and activates this residue, is charge-stabilized and the charge-stabilized leaving group is bound to the acyl group of the C-terminal carboxylic acid of the peptide. "Substrates" are understood here to be linear peptides on which a nucleophilic charge-stabilized leaving group according to the present invention is chemically bound. In this, charge-stabilized thio and hydroxy compounds are understood to be aromatic or heteroaromatic ring systems in which a hydroxy or thio group is bound to one of the ring atoms or on a carbon atom which is bound to the ring system, wherein the chemical structure of the aromatic or heteroaromatic system is chosen in such a way that a negative charge occurring on the thio or hydroxy group is stabilized. The method according to the present invention leads to higher yields of cyclic peptides and/or increases its yields and, for the first time, allows peptides such as fengycin, mycosubtilin, syringomycin and bacitracin to cyclize as well, which are not able to be cyclized with the methods according to the state of the art.

The provision of the substrates according to the present invention is carried out via the synthesis of the linear peptide with help from the standard methods of solid phase peptide synthesis known to persons skilled in the art, with subsequent coupling of the free carboxylic acid of the linear peptide (the free peptide acid) to the thiol or hydroxy leaving group according to the present invention, optional purification of the substrate obtained in this way according to the present invention, with subsequent reaction of the substrate obtained in this way according to the present invention with a peptide cyclase and purification of the cyclic peptides obtained in this way.

For this, 1 equivalent (eq) of the free peptide acid is reacted with 2 eq dicyclohexylcarbodiimide (DCC), 2 eq N-hydroxybenzotriazole (HOBt) and 10 eq of the respective leaving group and stirred for 30 min in THF. After addition of 0.5 eq potassium carbonate, the reaction is agitated for a further 2.5 h and then filtrated to remove precipitated dicyclohexylurea (DCU). The solvent is evaporated and the peptide is deprotected with 95% trifluoroacetic acid (TFA), 2.5% water and 2.5% triisopropylsilane for 3 h. The reaction mixture is then added to ice-cold diethyl ether, subsequent to which the substrate precipitates. This step represents purification, by which reaction byproducts are removed and leads to a substrate purity of up to 80%, which is generally satisfactory for a further reaction of the substrate with a peptide cyclase. Optionally, the purity of the substrate can be subsequently increased by means of preparative HPLC. If the linear peptide next to the C-terminal free COOH group has further free COOH groups within the peptide chain, such as e.g. COOH groups from glutamic acid and/or aspartic acid, then these non C-terminal free COOH groups must be protected before the reaction of the linear peptide with an activating reagent with a suitable orthogonal protective group, which must then be cleaved off after production of the substrate according to the present invention. Suitable protective groups and suitable methods of their removal are known to persons skilled in the art and can be read about, for example, in Theodora W. Greene and Peter G. M. Wuts, "Protective groups in organic synthesis," $2^{nd}$ Edition 1991, John Wiley & Sons Inc., New York/Chichester/Brisbane/Toronto/Singapore.

The purified substrate with the leaving group according to the present invention is then incubated with the respective peptide cyclase in the ratio of 1 (enzyme): 100 (substrate) in 25 mM HEPES, 50 mM NaCl at pH 7 and room temperature for 30-60 minutes. The production of the HEPES solution is known to persons skilled in the art and was described in J. Sambrook, E. F. Fritsch and T. Maniatis: *Molecular Cloning: A Laboratory Manual Vol. I-III*, Cold Spring Harbor Laboratory Press, 1982. The identification and quantification of the reaction product is carried out by means of analytical HPLC.

As an alternative to the activation reagent DCC, the substrates according to the present invention can also be reacted by reaction of the peptide acid with the respective leaving group in the presence of other reagents activating the C-terminus of the peptide acid. Equivalents are known and can be used without leaving the area protected by the patent claims. Hereby, the activation reagents known to persons skilled in the art include, for example, DCI (N,N-diisopropylcarbodiimide), PyClop (chlorotripyrrolidinophosphonium hexafluorophosphate), HBTU (2-(1H-benzotriazole-1-yl)-1,1,3,3-tetramethyluronium hexafluorophosphate), HATU (2-(7-aza-1H-benzotriazole-1-yl)-1,1,3,3,-tetramethyluronium hexafluorophosphate), HOSu (N-hydroxysuccinimide), TBTU (2-(1H-benzotriazole-1-yl)-1,1,3,3-tetramethylaminium tetrafluoroborate), T3P (propylphosphonic anhydride), BopCl (bis(2-oxo-3-oxazolidinyl)phosphonic chloride) and 3-Cl-I-pyridiniumiodide. Apart from HOBt listed above, the substances HOAt (1-hydroxy-7-azabenzotriazole) and HONB (N-hydroxy-5-norbornene-2,3-dicarboxylimide), which are known to persons skilled in the art, can also be used as coupling additives. It is known to persons skilled in the art that these reactions are effectively carried out with the addition of a base, such as e.g. DIPEA. Furthermore, different solvents for use in the methods mentioned are known to persons skilled in the art Skilled persons can produce these combinations of activation reagents, coupling additives, bases, and solvents themselves with their general knowledge and standard literature.

Charge-stabilized leaving groups are understood in the present invention to be chemical compounds which possess a thio or hydroxyl group and in which the free electron pair of the thiolate or hydroxylate ion released by the acylation reaction stands in conjugation with other electron pairs from, for example, but not exclusively, C=C or C=N double bonds or in which the thio or hydroxy group is bound to a carbon atom which is, for its part, bound to an aromatic or heteroaromatic ring. Such compounds are, e.g. oxo- and thio-aromatic, and oxo- and thio-heteroaromatic compounds, but also charge-stabilized aliphatic oxo and thio leaving groups. These leaving groups, such as e.g. thiophenol, phenol, 2,3,4,5,6-pentafluorophenol, mercaptoanisoles and thiocresols, 2-hydroxypyridine, 2-thiopyridine work in the acylation reaction of peptide cyclases which possess no similarity with the natural cofactor at all, and feature improved characteristics for in vitro cyclization reactions.

This is to be explained in the following, for example, but not exhaustively, with the example of thiophenol:

The thiophenol leaving group features, apart from the thiol function, no structural similarity with natural 4'-phosphopantetheine cofactor. The thiol function is directly bound to an aromatic phenyl ring. This structural characteristic causes a higher reactivity of this compound in relation to the leaving groups already described. During nucleophilic attack of the activated Ser (=serine) of the catalytic triad in the active center of the enzyme, this leaving group is released as a thiophenolate ion. The resulting negative charge at the sulfur atom can, in this, be delocalized by the adjacent phenyl ring very well.

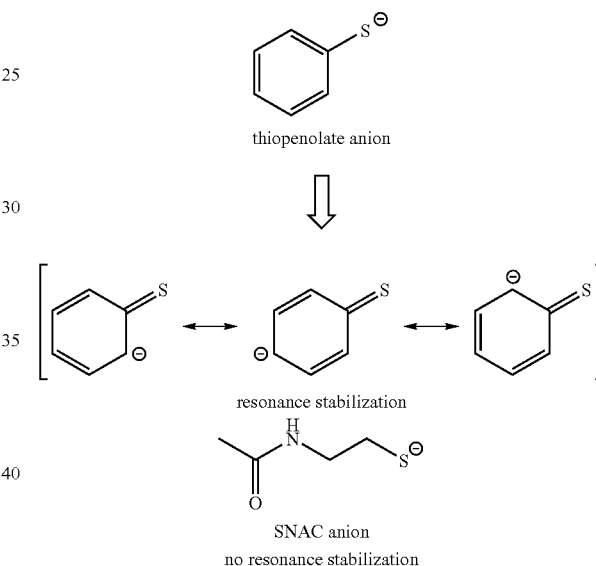

thiopenolate anion resonance stabilization

SNAC anion
no resonance stabilization

An increase and stabilization of the electron density of this kind does not occur with SNAC, CoA and Ppant leaving groups. In these cases, the negative charge remains localized at the sulfur atom. Since as a rule, however, the quality of a leaving group is proportional to its chemical stabilization, SNAC, CoA, and Ppant are worse leaving groups than thiophenol from a chemical viewpoint.

It is known to persons skilled in the art that the leaving ability and, therefore, the quality of a leaving group is dependent upon the ability of the leaving group to stabilize a negative charge. Stabilization of a charge is understood here by skilled persons to be the distribution of charges or partial charges over several atoms or bonds, so that this charge or partial charge is not localized at a unique atom or bond within a molecule. In this, two different possibilities for charge stabilization of organic molecules, which are generally called mesomeric or resonance effects (M effects) and inductive effects (I effects), are known to persons skilled in the art. Persons skilled in the art understand a mesomeric or resonance effect to be the quick and reversible moving around of π electron pairs, which occurs in systems which possess conjugated π bonds. It is known to persons skilled in the art that the mesomeric effect is effective over large distances and, therefore, on many bonds when a corresponding extended conjugated π system exists. In ring compounds with conjugated π systems, substituents also take part in the mesomerism, as long as they have free π electron pairs at their disposal or can absorb these. If a charge is to be stabilized in a substituted ring compound with a conjugated π system and substituents with mesomeristic capacities, then it depends on the position of the substituents to one another if and which of these substituents in fact take part in charge-stabilization by mesomerism. This is known to persons skilled in the art.

If an atom possesses a higher electronegativity and, therefore, a stronger attraction to the binding electrons than its neighboring atom which is bound to it by a σ bond, or if an atom is bound with further atoms or atom groups which have an electron withdrawing effect, the electron cloud of the σ bond mentioned here will be moved in the direction of electron withdrawal, i.e. polarized. This polarization of a σ bond is described as a partial charge, since it concerns a slight movement of electron clouds here and this movement does not lead to the occurrence of integer multiples of the elementary charge at a certain atom. The polarization of σ bonds caused by different electronegativities and/or different electron withdrawal of atoms and atom groups is described as an inductive effect by persons skilled in the art. That the inductive effect is the biggest for neighboring bonds and decreases quickly with increasing distance to the atom or atom group which causes it is known to persons skilled in the art. This can be read about, e.g. in Michael B. Smith & Jerry March: *March's Advanced Organic Chemistry. Reactions, Mechanisms, and Structure.* 5th Edition 2000, John Wiley & Sons Inc., New York/Chichester/Brisbane/Toronto/Singapore.

Persons skilled in the art differentiate between positive and negative mesomeric or inductive effects, respectively. Such an effect is described as positive when it increases the electron density in the form of a charge or partial charge on an atom or atom group (+M effect, +I effect), negative when it decreases the electron density (−M effect, −I effect). If several substituents are located, for example, on an aromatic system, they exert their M effects and I effects independently of one another and can have an intensifying, but also an opposing effect amongst each other in relation to charge stabilization on a certain atom. As a rule, mesomeric effects are stronger than inductive. Therefore, in the invention at hand, such charge-stabilized leaving groups are preferably chosen, in which a hydroxy or thio group is bound to one of the ring atoms of an aromatic, heteroaromatic or araliphatic system or to a carbon atom which is bound to the ring system, wherein the chemical structure of the aromatic, heteroaromatic or araliphatic system is so chosen that the sum of the mesomeric and inductive effects of the groups obtained exerts an electron withdrawal on the thiolate or hydroxylate ion and thus stabilizes the negative charge thereof.

A further important criterion for the quantification of the leaving group quality is the $pK_A$ value of a chemical compound: the higher the $pK_A$ value, the worse the respective leaving group is. CoA, Ppant and SNAC have $pK_A$ values of 10-11, while thiophenol features a $pK_A$ value of 8. From that, it can be said that thiophenol can overcompensate for its lacking structural consistency with the natural phosphopantetheine cofactor surprisingly and contrary to the state of the art by its high chemical reactivity, which is also true for other aromatic, heteroaromatic and charge-stabilized araliphatic thiol or hydroxyl compounds. In this, such charge-stabilized aromatic, heteroaromatic and araliphatic thiol and hydroxyl compounds whose $pK_A$ value is smaller or equal to 10, preferably smaller or equal to 8, are used advantageously as leaving groups. The ring systems of the aromatic, heteroaromatic and araliphatic thiol and hydroxy compounds according to the present invention can be substituted by one or more substituents with positive or negative inductive or mesomeric effects, wherein the totality of the effects of all the substituents at hand causes an electron withdrawing and thus stabilizing force on the thiolation or hydroxylation released during the enzymatic cyclization.

In the use of charge-stabilized thiol and hydroxy compounds, such enzymes also show cyclization activity which were classified as inactive with the use of the leaving groups known so far (approx. ⅔ of all examined so far). Enzymes which also cyclize during use of SNAC as a leaving group show better kinetic properties with $k_{cat}/K_M$ values increased up to 15 times with constant regioselectivity and stereoselectivity, when thiophenol derivatives are used in place of SNAC leaving groups. This was demonstrated with the example of surfactin thiophenol (see FIG. 4). Surfactin likewise shows improved reaction rates during cyclization when o-mercapto anisole, m-mercapto anisole, or p-mercapto anisole or o-thiocresole, m-thiocresole, or p-thiocresole are used as leaving group.

The catalysis by peptide cyclases can be broken down into two partial steps:
The first partial step is the formation of the peptidyl-O-TE-intermediate through the acylation of the activated Ser residue of the catalytic triad.
The second partial step consists of the deacylation of the Ser residue by a functional group of the bound peptide chain as an internal nucleophile.

Thioester-bound leaving groups can exclusively influence the catalytic efficiency of the first partial step: the formation of the peptidyl-O-TE intermediate. Experiments with the new leaving group thiophenol confirm this (see FIG. 4 to FIG. 6). A mutation within the active center of the enzyme shows no activity which confirms the acylation by the leaving group and the following enzymatic cyclization.

The following aromatic, heteroaromatic, and araliphatic basic elements serve as charge-stabilized leaving groups:

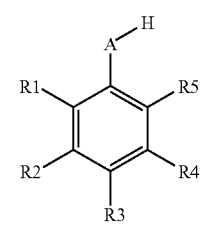

(I)

with
A=O, S and
as well as R1, R2, R3, R4 and R5, which are independent of one another:
—NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, -heteroaryl,
wherein
L=-alkyl, -alkenyl, -cycloalkyl, -cycloalkenyl, -heteroalkyl, -heterocycloalkyl, -aryl, -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, phosphorus; the heterocyclic groups stand for a residue with 1 to 20 carbon atoms wherein up to 5 carbon atoms are substituted by heteroatoms chosen from the group nitrogen, oxygen, sulfur, phosphorus; aryl stands for an aromatic residue with 5 to 20 carbon atoms and heteroaryl for a corresponding aromatic residue in which up to 5 carbon atoms are substituted by heteroatoms chosen from the group nitrogen, oxygen, sulfur, phosphorus, wherein the conditions are chosen in such a way that, in temperatures lower than 200° C. and atmospheric pressure, no explosive substances are formed and the compounds comprised of linear peptides, and the leaving groups according to the present invention bound to those, are not hydrolytically cleaved in these conditions,

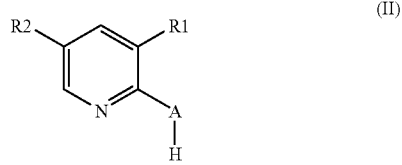

(II)

with
A=O, S and
as well as R1 and R2, which are independent of one another:
—$NO_2$, —CN, —F, —Cl, —Br, —I, —$CH_2Cl$, —$SO_3H$, —H, —$NH_3^+$, —$NL_3^+$, —C(=O)L, —C(=O)Het, —$O^-$, —$NL_2$, —$NH_2$, —OL, —OH, —NHC(=O)L, —OC(=O)L, —SL, —$CO_2^-$, -alkyl, -alkenyl, -cycloalkyl, -cycloalkenyl, -heteroalkyl, -heterocycloalkyl, -aryl, -heteroaryl,
wherein
L=-alkyl, -alkenyl, -cycloalkyl, -cycloalkenyl, -heteroalkyl, -heterocycloalkyl, -aryl, -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, phosphorus; the heterocyclic groups stand for a residue with 1 to 20 carbon atoms wherein up to 5 carbon atoms are substituted by heteroatoms chosen from the group nitrogen, oxygen, sulfur, phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, phosphorus, wherein the conditions are chosen in such a way that, in temperatures lower than 200° C. and atmospheric pressure, no explosive substances are formed and the compounds comprised of linear peptides and the leaving groups according to the present invention bound to those are not hydrolytically cleaved in these conditions, whereby it is known to persons skilled in the art, that substituents bound to C-4 or C-6 of the pyridine ring do not cause a charge stabilization of the hydroxy or thiol substituent that is bound to C-2,

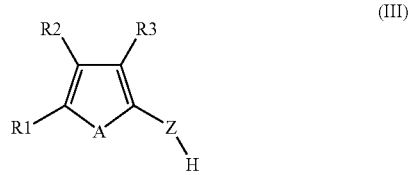

(III)

with
A=O, S, and
z=O, S,
as well as R1, R2, and R3, which are independent of one another:
—$NO_2$, —CN, —F, —Cl, —Br, —I, —$CH_2Cl$, —$SO_3H$, —H, —$NH_3^+$, —$NL_3^+$, —C(=O)L, —C(=O)Het, —$O^-$, —$NL_2$, —$NH_2$, —OL, —OH, —NHC(=O)L, —OC(=O)L, —SL, —$CO_2^-$, -alkyl, -alkenyl, -cycloalkyl, -cycloalkenyl, -heteroalkyl, -heterocycloalkyl, -aryl, -heteroaryl,
wherein
L=-alkyl, -alkenyl, -cycloalkyl, -cycloalkenyl, -heteroalkyl, -heterocycloalkyl, -aryl, -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, phosphorus; the heterocyclic groups stand for a residue with 1 to 20 carbon atoms wherein up to 5 carbon atoms are substituted by heteroatoms chosen from the group nitrogen, oxygen, sulfur, phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, phosphorus, wherein the conditions are chosen in such a way that, in temperatures lower than 200° C. and atmospheric pressure, no explosive substances are formed and the compounds comprised of linear peptides and the leaving groups according to the present invention bound to those are not hydrolytically cleaved in these conditions,

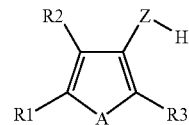

(IV)

with
A=O, S, and
Z=O, S,
as well as R1, R2, and R3, which are independent of one another:
—$NO_2$, —CN, —F, —Cl, —Br, —I, —$CH_2Cl$, —$SO_3H$, —H, —$NH_3^+$, —$NL_3^+$, —C(=O)L, —C(=O)Het, —$O^-$, —$NL_2$, —$NH_2$, —OL, —OH, —NHC(=O)L, —OC(=O)L, —SL, —$CO_2^-$, -alkyl, -alkenyl, -cycloalkyl, -cycloalkenyl, -heteroalkyl, -heterocycloalkyl, -aryl, -heteroaryl,
wherein
L=-alkyl, -alkenyl, -cycloalkyl, -cycloalkenyl, -heteroalkyl, -heterocycloalkyl, -aryl, -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, phosphorus; the heterocyclic groups stand for a residue with 1 to 20 carbon atoms wherein up to 5 carbon atoms are substituted by heteroatoms chosen from the group nitrogen, oxygen, sulfur, phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, phosphorus, wherein the conditions are chosen in such a way that, in temperatures lower than 200° C. and atmospheric pressure, no explosive substances are formed and the compounds comprised of linear peptides and the leaving groups according to the present invention bound to those are not hydrolytically cleaved in these conditions,

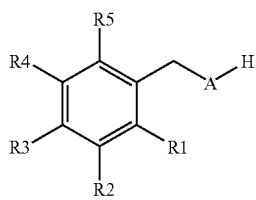

(V)

with
A=O, S and
as well as R1, R2, R3, R4 and R5, which are independent of one another:
—$NO_2$, —CN, —F, —Cl, —Br, —I, —$CH_2Cl$, —$SO_3H$, —H, —$NH_3^+$, —$NL_3^+$, —C(=O)L, —C(=O)Het, —$O^-$, —$NL_2$, —$NH_2$, —OL, —OH, —NHC(=O)L, —OC(=O)L, —SL, —$CO_2^-$, -alkyl, -alkenyl, -cycloalkyl, -cycloalkenyl, -heteroalkyl, -heterocycloalkyl, -aryl, -heteroaryl,
wherein
L=-alkyl, -alkenyl, -cycloalkyl, -cycloalkenyl, -heteroalkyl, -heterocycloalkyl, -aryl, -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, phosphorus; the heterocyclic groups stand for a residue with 1 to 20 carbon atoms wherein up to 5 carbon atoms are substituted by heteroatoms chosen from the group nitrogen, oxygen, sulfur, phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, phosphorus, wherein the conditions are chosen in such a way that, in temperatures lower than 200° C. and atmospheric pressure, no explosive substances are formed and the compounds comprised of linear peptides and the leaving groups according to the present invention bound to those are not hydrolytically cleaved in these conditions, Furthermore, these leaving groups can also replace the natural cofactor for other artificial reactions of the non-ribosomal peptide synthetase in vitro. Such a reaction is represented by the condensation reaction to form a peptide bond, catalyzed by the condensation domain (C domain) which also operates with thioester-bound substrates.

Surprisingly, and in contradiction with the technical state of the art, it was found that the recognition of the substrates by the respective enzyme plays no role whatsoever. Thus, the invention at hand provides a new and, for the average person skilled in the art, surprising further development of the method described in US 2002/0192773 A1 for the enzymatic production of macrocyclic molecules, in which purified, isolated thioesterase domains derived from a PKS or NRPS multidomain system are reacted with a substrate.

The substrates in question include linear peptides and lipopeptides with 5 to 22 monomeric units, such as e.g. amino acids. Substrates are, for example, fengycin, mycosubtilin, bacillibactin, CDA, surfactin, bacitracin or syringomycin and further substrates which are already described in US 2002/0192773 A1, as well as prystinamycin, whereby the substrates indicated additionally feature a leaving group according to the present invention. Several of these substrates are depicted in the following:

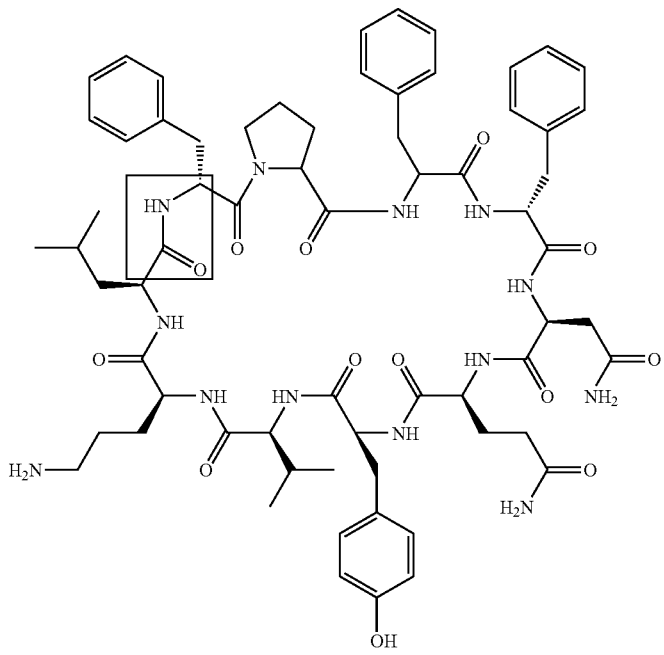

Tyrocidin (Antibiotikum)

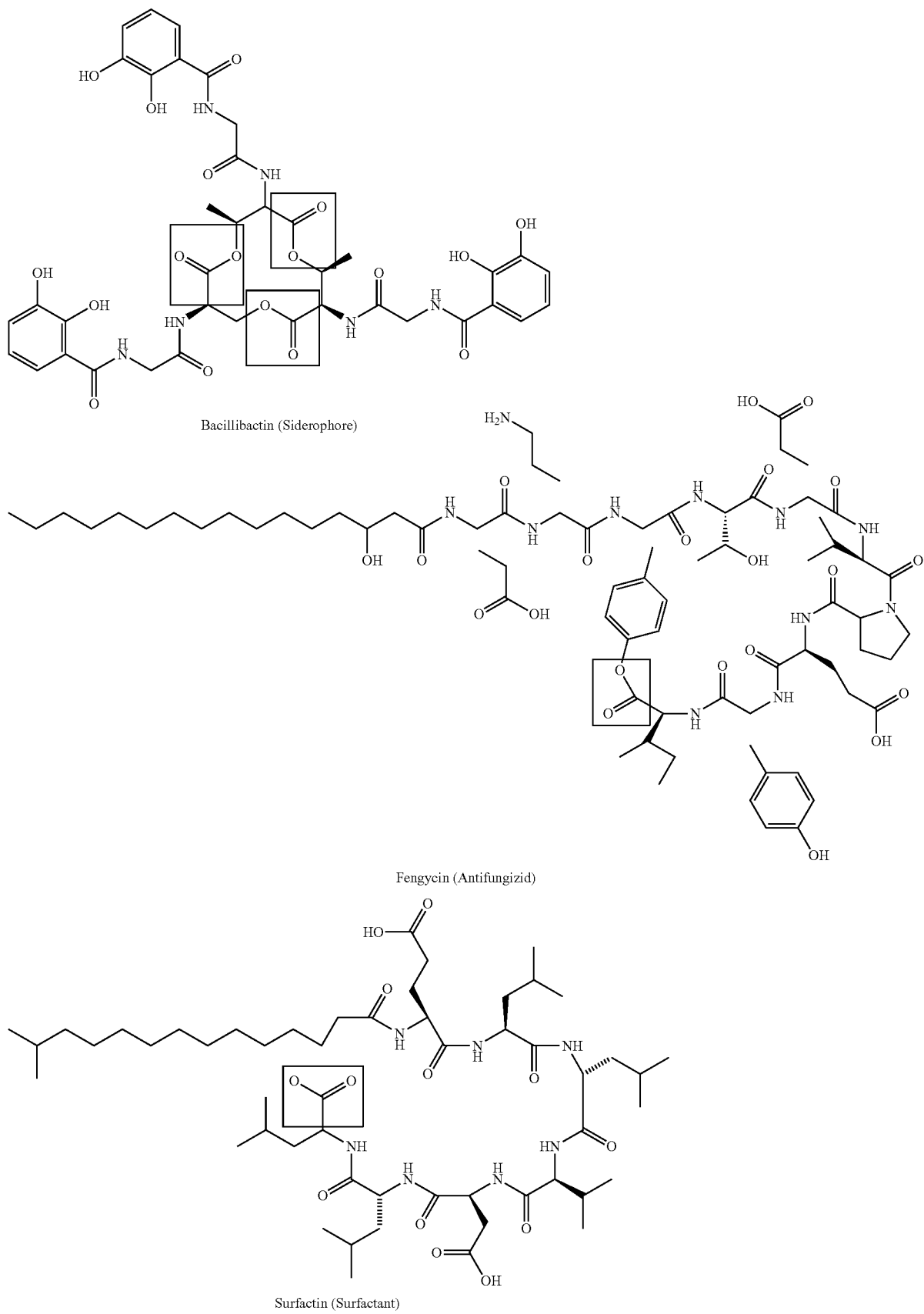

-continued
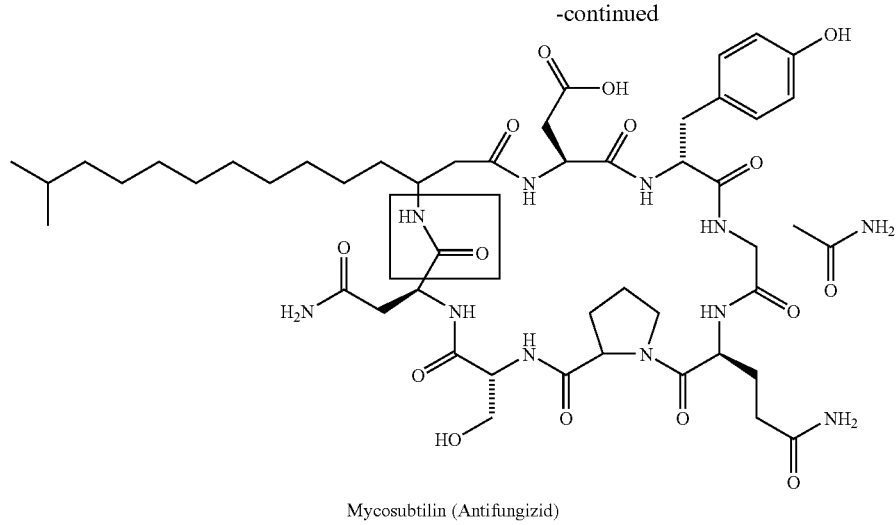
Mycosubtilin (Antifungizid)
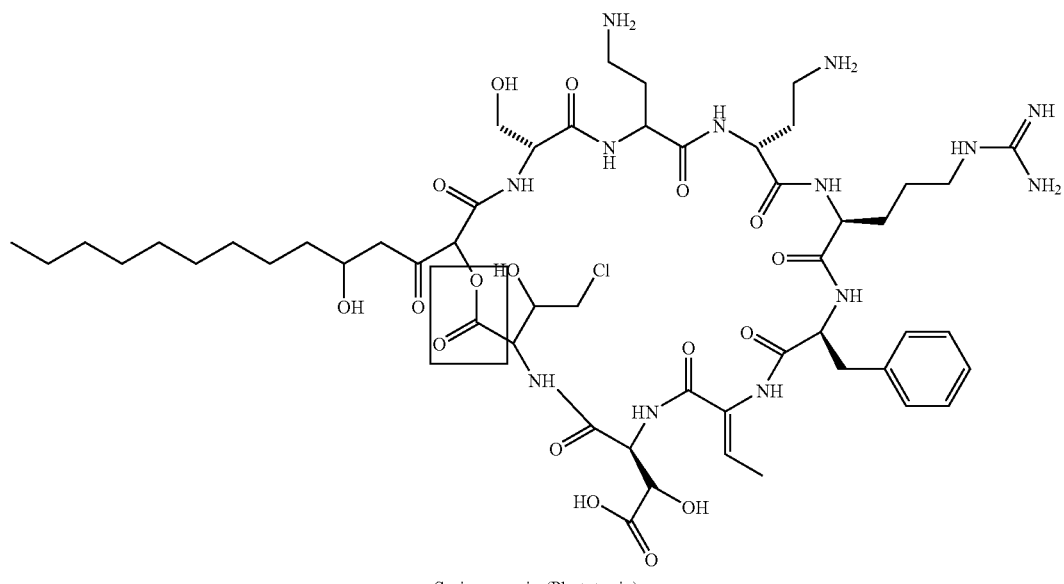
Syringomycin (Phytotoxin)
Bioactive Peptides
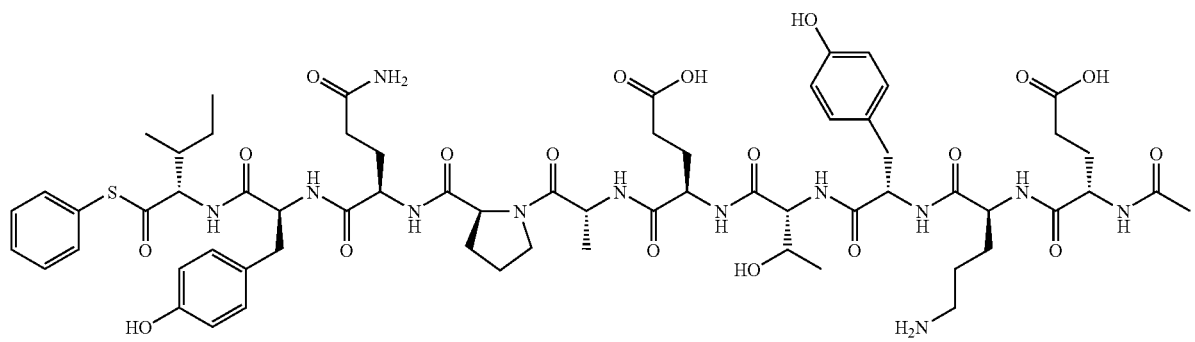

Structure of a Fengycin-Thiophenol Substrate

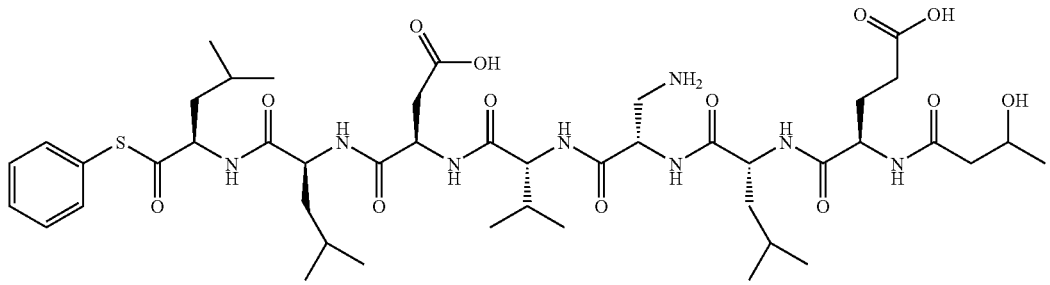

Structure of a Surfactin-Thiophenol Substrate

The method according to the present invention also provides, in comparison with the state of the art, an improvement for such linear peptides which could already be cyclized by methods known to persons skilled in the art, since the method according to the present invention accelerates the reaction rate of the cyclization and/or leads to higher yields of the cyclic peptides.

The enzymes in question include purified, isolated thioesterase domains or peptide cyclases from NRPS or PKS systems, such as e.g. the corresponding domains or cyclases of fengycin, mycosubtilin, bacillibactin, CDA, surfactin, bacitracin, syringomycin, tyrocidin, prystinamycin and all other peptide cyclases, thioesterases and purified, isolated thioesterases listed in US 2002/0192773 A1.

The linear peptide contains proteinogenic and non-proteinogenic amino acids in its backbone. Residues and/or functional groups, which do not derive from amino acids, can also be embedded in this backbone, such as e.g. saturated or unsaturated carbon spacers. The residues and/or functional groups facultatively embedded in the backbone were already described in US 2002/0192773 A1. For this, the leaving group according to the present invention is attached either to the C-terminal carboxylic acid group or to a side chain carboxylic acid.

The leaving group technology according to the present invention can be used for the production of substance libraries for cyclic peptides and proteins, producing new substrate variants of new structurally important molecules (for example, fengycin, mycosubtilin, syringomycin, CDA, etc.), which have so far shown no or little activity with the usual leaving group SNAC, and testing them for improved biological properties (antibiotic, antiviral, antifungal, cytostatic). The substrate variants are produced by combinatorial solid phase peptide synthesis and provided with the new leaving groups according to the aforementioned, general instruction. In this, a substance library for peptide antibiotics adapted to target cells is preferably produced, whereby cyclic peptide antibiotics which were produced with the help of the method according to the present invention are meant.

The method according to the present invention can be used for the production of cyclization kits which provide means for the coupling of charge-stabilized leaving groups according to the present invention as well as peptide cyclases, so that linear peptides can be reacted with the leaving groups made available, at first to form substrates according to the present invention and subsequently with the peptide cyclases made available, to form cyclic peptides. The producer of the kits according to the present invention knows from general knowledge how to produce, formulate and store the single components of the kit, e.g. buffers.

The cyclic peptides and proteins produced by the method according to the present invention can be used as pharmaceuticals for patients for the therapy, diagnosis and prophylaxis of diseases in which bacterial and/or viral infections arise. Furthermore, the cyclic peptides and proteins according to the present invention can be used as pharmaceuticals for patients for the therapy, diagnosis and prophylaxis of tumor diseases as well as in transplantation medicine, provided that they feature cytostatic and/or immunosuppressive properties. The term patient refers equally to humans and vertebrates. Thus, the pharmaceuticals can be used both in human and veterinary medicine. Pharmaceutically acceptable compositions of compounds according to the claims can be available as dimers up to oligomers or as salts, esters, amides, or "prodrugs" thereof, provided that, according to reliable medical evaluation, they do not cause excessive toxicity, irritations or allergic reactions to patients. The therapeutically effective compounds according to the present invention can be administered to patients as part of a pharmaceutically acceptable composition either in oral, rectal, parenteral, intravenous, intramuscular, subcutaneous, intracisternal, intravaginal, intraperitoneal, intravascular, intrathecal, intravesical, topical, local form (powder, salves or drops) or in aerosol form, wherein the intravenous, subcutaneous, intraperitoneal or intrathecal administration can be carried out continuously by means of a pump or dosage unit. Forms of dosage for local administration of the compounds according to the present invention include salves, powders, suppositories, sprays and inhalants. Hereby, the active component is mixed under sterile conditions with a physiologically acceptable carrier and possible stabilizing and/or preserving additives, buffers, diluents and propellants according to need.

EMBODIMENTS

Embodiment 1

Production of the Fengycin-Thiophenol Substrate as well as Cyclization

The linear fengycin substrate is first produced according to standard methods of peptide solid phase synthesis. The peptide sequence is: Acetyl-Glu-D-Orn-Tyr-D-Thr-Glu-D-Ala-Pro-Gln-D-Tyr-Ile-COOH. In the next step, 0.1 mMol DCC, 0.1 mMol HOBt and 0.5 mMol of thiophenol are added to 0.05 mMol of the peptide and dissolved in 2 ml THF. The mixture is stirred for 30 min at RT, and 0.05 mMol of potassium carbonate is added. The mixture is stirred for a further 2.5 h at RT, subsequently solid DCH is removed by filtration and the solvent is evaporated. The deprotection of the peptide side chains is carried out for 3 h in 2 ml of 95% TFA, 2.5% water and 2.5% triisopropylsilane. The mixture is then poured into 50 ml of ice-cold diethyl ether and the resulting solid is separated by centrifugation. The purification of the solid is carried out by means of preparative HPLC with a Nucleodur $C_{18}$ column (pore size 100 Å, particle size 7 µM, diameter 10 mm, length 250 mm, Macherey-Nagel) with a gradient of 10% acetonitrile in water/0.1% TFA up to 70% acetonitrile in water/0.1% TFA in 40 min at a flow rate of 6 ml/min. The retention time of the cyclized fengycin (see FIG. 1) is 19 min. The yield is between 70 and 80%.

The products are tested for purity and identity with LC-MS and MALDI-TOF mass spectrometry.

The cyclization of the linear fengycin-thiophenol substrate is carried out in an aqueous cyclization buffer comprised of 2-[4-(2-hydroxyethyl)-1-piperazinyl]-ethane sulfonic acid (HEPES, 25 mM) and sodium chloride (NaCl, 50 mM) at pH 7 in a total volume of 50 µL. The substrate concentration is 100 µM for standard cyclization reactions. The cyclization reaction is initiated by the addition of recombinant fengycin TE at an end concentration of 5 µM and stopped by the addition of 35 µL of 4% trifluoroacetic acid (TFA) in water after 4 hours. Subsequently, the reaction products are examined by means of HPLC with a Nucleodur $C_{18}$ column (pore size 100 Å, particle size 3 µM, diameter 10 mm, length 250 mm, Macherey-Nagel) and a gradient of 30% acetonitrile in water/0.1% TFA up to 60% acetonitrile in water/0.1% TFA in 35 min at a flow rate of 0.4 mL/min at 40° C. The identity of the products is confirmed by ESI mass spectrometry. Pure cyclized fengycin can be obtained by means of preparative HPLC.

Embodiment 2

Production and Purification of the Fengycin-Benzylmercaptane Substrate as well as Cyclization Production, purification and cyclization of the fengycin-benzylmercaptane substrate were carried out analogously to embodiment 1, wherein in embodiment 20.05 mMol benzylmercaptane is used instead of 0.05 mMol thiophenol. The yield of the cyclized fengycin is approx. 70%.

Embodiment 3

Production and Purification of Further Fengycin Substrates as well as Cyclization Fengycin is reacted with further leaving groups as described in embodiments 1 and 2. These are 2-mercaptopyridine, p-nitrothiophenol and pentafluorothiophenol. The cyclization of these fengycin substrates is carried out analogously to embodiment 1 and yields significantly higher percentages of the not enzymatically catalyzed cyclization product or the hydrolyzed product than in the case of using thiophenol or benzylmercaptane, respectively.

TABLE 1

| compound | species | ionization method | mass observed (mass calculated) (Da) |
|---|---|---|---|
| fengycin-thiophenol | [M + H]⁺ | ESI | 1361.40 (1361.60) |
| surfactin-thiophenol | [M + H]⁺ | ESI | 965.40 (965.49) |
| CDA-thiophenol | [M + H]⁺ | ESI | 1519.30 (1519.5) |

TABLE 1-continued

| compound | species | ionization method | mass observed (mass calculated) (Da) |
|---|---|---|---|
| syringomycin-thiophenol | [M + H]⁺ | ESI | 1175.60 (1175.54) |

The linear peptides fengycin, surfactin, CDA and syringomycin are reacted with thiophenol as described in embodiment 1 and subsequently enzymatically cyclized. Tab. 1 shows the results of the mass spectrometric measurement of the substances yielded according to the present invention.

LIST OF REFERENCE NUMERALS

FIG. 1: HPLC of the Reaction of Fengycin-thiophenol with the Fengycin-peptide Cyclase HPLC-MS with a reversed phase Nucleodur $C_{18}$ column (Macherey and Nagel, 250/3, pore diameter: 100 Å, particle size: 3 µm) with the following gradient: 0-35 min, 30-60% acetonitrile/0.1% TFA in water/0.1% TFA; 0.4 mL/min, 40° C. 1 shows the control reaction with a mutated (inactivated) enzyme. 2 shows the incubation with the native enzyme (active). Su=substrate, Cy=cyclic product, Hy=hydrolyzed product.

Figure 2:
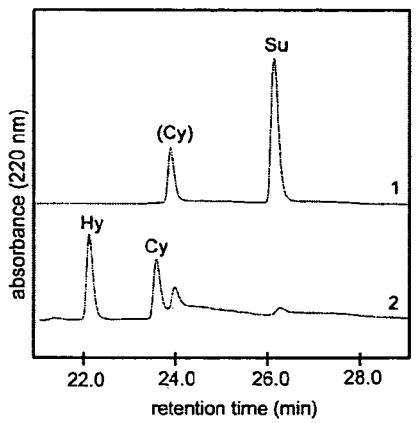

FIG. 2: HPLC of the Reaction of Surfactin-Thiophenol with the Surfactin-peptide Cyclase HPLC-MS with a reversed phase Nucleodur $C_{18}$ column (Macherey and Nagel, 250/3, pore diameter: 100 Å, particle size: 3 µm) with the following gradient: 0-35 min, 30-60% acetonitrile/0.1% TFA in water/0.1% TFA; 0.4 mL/min, 40° C. 1 shows the control reaction without enzyme. 2 shows the incubation with the native enzyme (active). Su=substrate, Cy=cyclic product, Hy=hydrolyzed product, (Cy) non-enzymatically catalyzed amino side group within the peptide sequence on position 3 (Dap).

Figure 3:
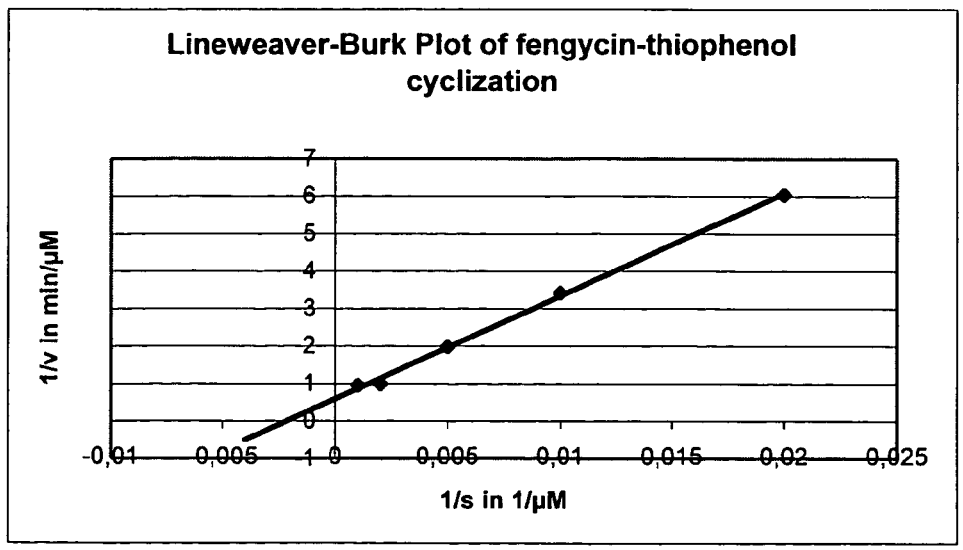

FIG. 3: Fengycin-peptide Cyclase

5 µM of the recombinated fengycin-peptide cyclase, which showed no cyclization activity in previous experiments with conventional SNAC-substrates, is incubated with 100 µM fengycin-thiophenol for 10, 30, 40, 50, 60 min at room temperature in 25 mM HEPES, 50 mM NaCl at pH 7 in a total volume of 50 µL. With this measurement, the linear range for further kinetic studies is determined. The reactions are stopped by the addition of 35 µL TFA (4% in water) and examined by analytic HPLC with a Nucleodur $C_{18}$ column (Macherey and Nagel, 250/3, pore diameter: 100 Å, particle size: 3 µm) with the following gradient: 0-35 min, 30-60% acetonitrile/0.1% TFA in water/0.1% TFA; 0.4 mL/min, 40° C. Kinetic examinations are carried out at different points in time at substrate concentrations of 50 µM up to 1000 µm and the kinetic parameters KM and kcat are taken from the Lineweaver-Burk plot. For fengycin-thiophenol, a $K_M$ of 461 µm and a $k_{cat}$ of 0.33 min$^{-1}$ result from the cyclization reaction.

Figure 4:
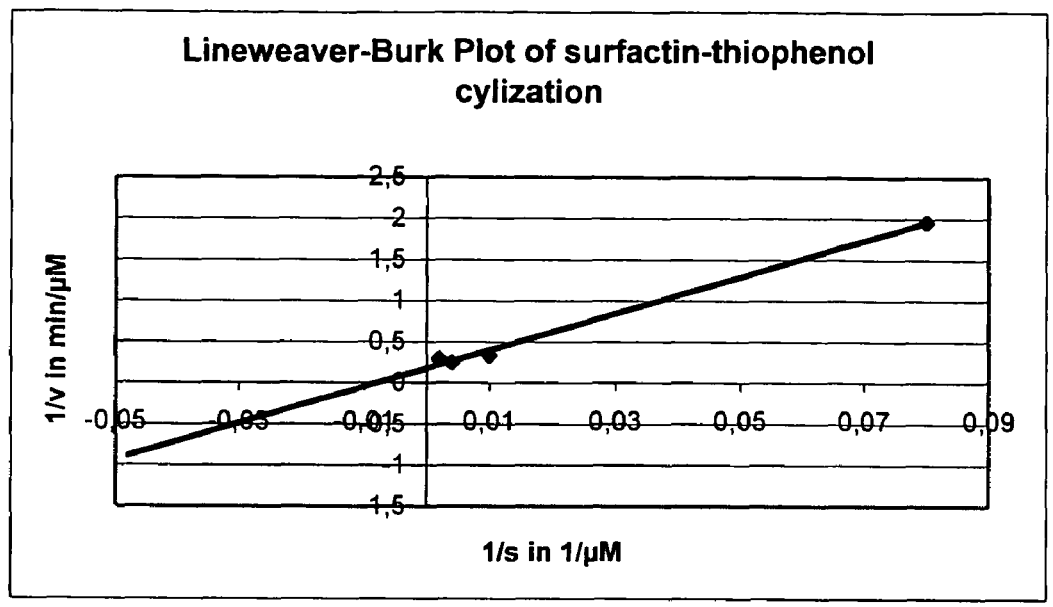

FIG. 4: Surfactin-peptide Cyclase

In the case of surfactin-peptide cyclase, kinetic reference data with a SNAC-substrate exists. In the case of surfactin-thiophenol, a $K_M$ of 126 µm and a kcat of 5.6 min$^{-1}$ are determined for the cyclization reaction, which corresponds to a $k_{cat}/K_M$ value of 0.04 µm$^{-1}$ min$^{-1}$. Compared with that is the kinetic efficiency of surfactin-SNAC, represented by the $k_{cat}/K_M$ value 0.0029 µm$^{-1}$ min$^{-1}$, 14 times less than with surfactin-thiophenol.

Figure 5:
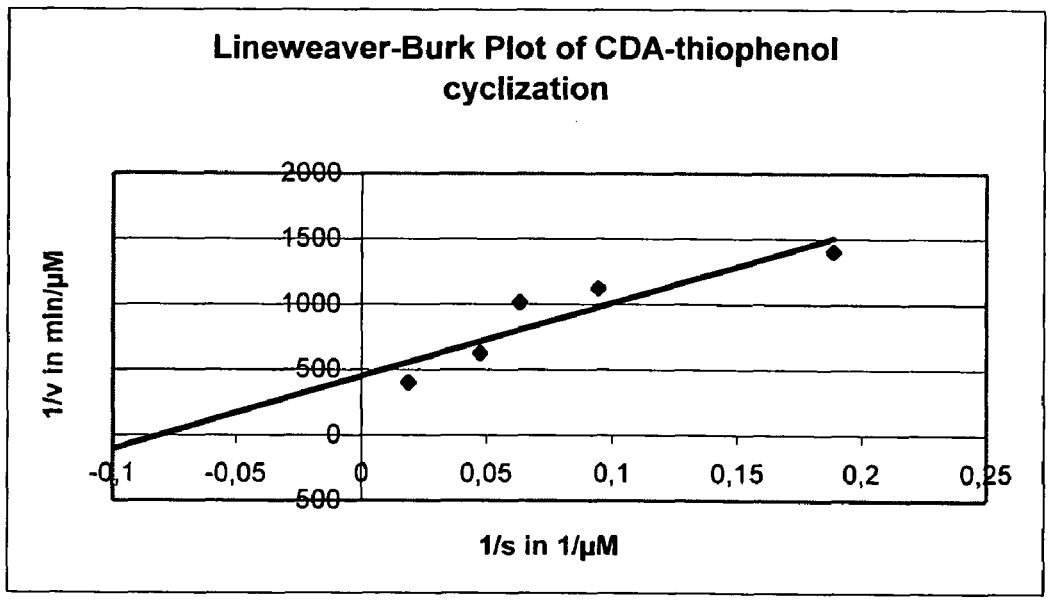

FIG. 5: CDA Peptide Cyclase

A similar result is obtained for the cyclization of CDA-thiophenol with the "calcium dependent antibiotic" peptide cyclase (CDA). The $K_M$ value for the thiophenol substrate is 10.7 μm, and the $k_{cat}$ value amounts to 0.21 $min^{-1}$. The kinetic efficiency of the thiophenol substrate, with a $k_{cat}/K_M$ value of 0.02 $μm^{-1} min^{-1}$ is 10 times larger than in comparison with the $k_{cat}/K_M$ value of the SNAC substrate ($k_{cat}/K_M$=0.0021 $μm^{-1} min^{-1}$).

Figure 6:
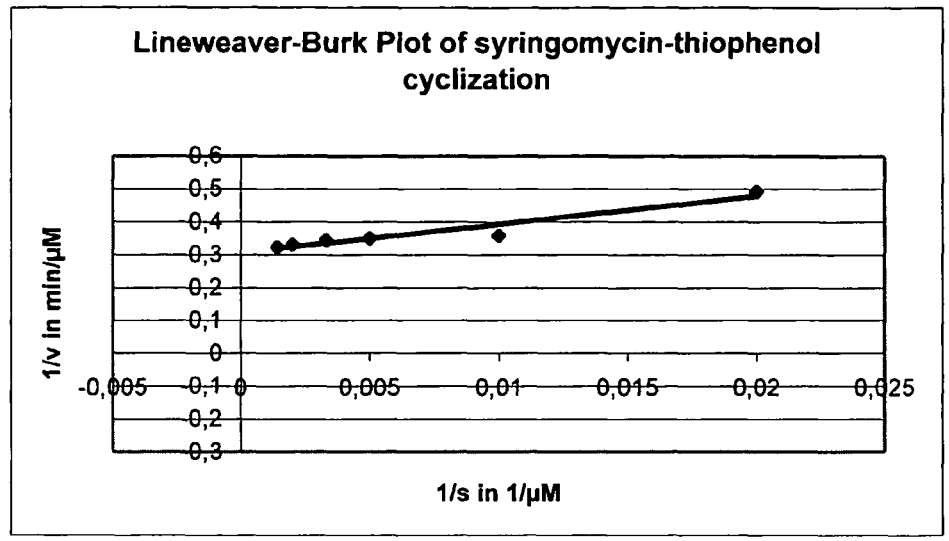

FIG. 6: Syringomycin Peptide Cyclase

In the case of syringomycin peptide cyclase, no kinetic reference data with a SNAC substrate exists, as the SNAC substrate showed no activity in previous experiments. In the case of syringomycin-thiophenol, a $K_M$ of 32.9 μM and a $k_{cat}$ of 0.805 $min^{-1}$ are determined for the cyclization reaction, which corresponds to a $k_{cat}/K_M$ value of 0.024 $μM^{-1} min^{-1}$.

Figure 7:
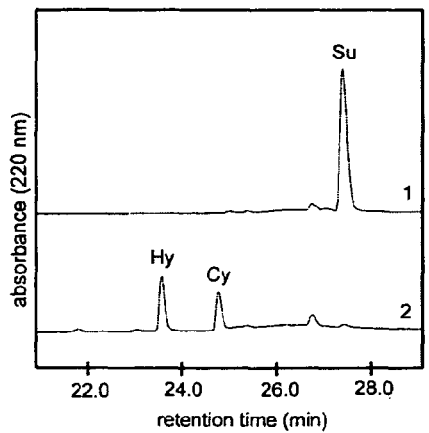

FIG. 7: HPLC of the Reaction of Surfactin-2-thiocresole with the Surfactin Peptide Cyclase HPLC-MS with a reversed phase Nucleodur $C_{18}$ column (Macherey and Nagel, 250/3, pore diameter: 100 Å, particle size: 3 μm) with the following gradient: 0-35 min, 30-60% acetonitrile/0.1% TFA in water/0.1% TFA; 0.4 mL/min, 40° C. 1 shows the control reaction with a mutated (inactivated) enzyme. 2 shows the incubation with the native enzyme (active). Su=substrate, Cy=cyclic product, Hy=hydrolized product.

Figure 8:
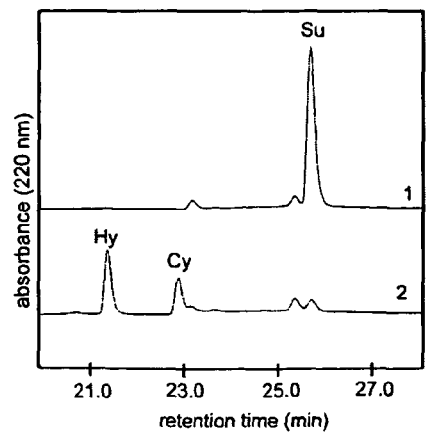

FIG. 8: HPLC of the Reaction of Surfactin-4-methoxythiophenol with the Surfactin Peptide Cyclase HPLC-MS with a reversed phase Nucleodur $C_{18}$ column (Macherey and Nagel, 250/3, pore diameter: 100 Å, particle size: 3 μm) with the following gradient: 0-35 min, 30-60% acetonitrile/0.1% TFA in water/0.1% TFA; 0.4 mL/min, 40° C. 1 shows the control reaction with a mutated (inactivated) enzyme. 2 shows the incubation with the native enzyme (active). Su=substrate, Cy=cyclic product, Hy=hydrolized product.

The invention claimed is:

1. Method for the production of cyclic peptides, in which a peptide cyclase is brought in contact with a linear peptide,
    the linear peptide contains an acyl residue, which is activated by a nucleophilic leaving group bound chemically with this acyl residue,
    the activated acyl residue of the linear peptide selectively acylates the center of the peptide cyclase, wherein the nucleophilic leaving group is cleaved off during formation of the cyclic peptide and
    cyclic peptides with rings of at least 5 atoms are formed, wherein
    the nucleophilic leaving group, which is chemically bound to the acyl residue of the linear peptide and which activates the latter, is charge-stabilized and
    the charge-stabilized leaving group is bound to the acyl group of the C-terminal carboxylic acid group.

2. The method for the production of cyclic peptides according to claim 1, wherein the charge-stabilized leaving groups are aromatic, heteroaromatic or araliphatic compounds, on which a hydroxy or thio group is bound to one of the ring atoms or to a carbon atom bound to the ring system.

3. The method for the production of cyclic peptides according to claim 1, wherein the peptide cyclase is a NRPS (non-ribosomal peptide synthetase) or PKS (polyketide synthetase) cyclase.

4. The method for the production of cyclic peptides according to claim 1, wherein the linear peptide contains proteinogenic and/or non-proteinogenic amino acids in its backbone, whereby residues which do not derive from amino acids can also be embedded in the backbone.

5. The method for the production of cyclic peptides according to claim 1, wherein the charge-stabilized leaving group is a compound of the formula

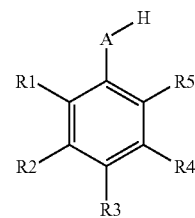

(I)

wherein the following applies:
    A is selected from O and S,
    and whereby R1, R2, R3, R4 and R5 are independent of one another and are selected from:
    -NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, and -heteroaryl,
    wherein
    L is selected from: -alkyl, -alkenyl, -cycloalkyl, -cycloalkenyl, -heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic group stands for a residue with 1 to 20 carbon atoms wherein up to 5 carbon atoms are substituted by heteroatoms chosen from the group nitrogen, oxygen, sulfur, phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus.

6. The method for the production of cyclic peptides according to claim 1, wherein the charge-stabilized leaving group is a compound of the formula

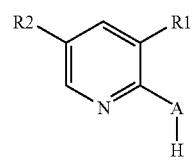

(II)

wherein the following applies:
    A is selected from O and S
    and whereby R1 and R2 are independent of one another and are selected from:
    -NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, and -heteroaryl,
    wherein
    L is selected from -alkyl, -alkenyl, -cycloalkyl, -cycloalkenyl, -heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus.

7. The method for the production of cyclic peptides according to claim 1, wherein the charge-stabilized leaving group is a compound of the formula

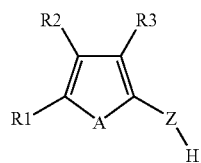

(III)

wherein the following applies:

A is selected from 0 and S and

Z is selected from 0 and S, and whereby R1, R2, and R3 are independent of one another and are selected from:

-NO$_2$, —CN, —F, —Cl, —Br, —I, —CH$_2$Cl, —SO$_3$H, —H, —NH$_3^+$, —NL$_3^+$, —C(═O)L, —C(═O)Het, —O$^-$, —NL$_2$, —NH$_2$, —OL, —OH, —NHC(═O)L, —OC(═O)L, —SL, —CO$_2^-$, -alkyl, -alkenyl, -cycloalkyl, -cycloalkenyl, -heteroalkyl, -heterocycloalkyl, -aryl, and -heteroaryl, wherein L is selected from -alkyl, -alkenyl, -cycloalkyl, -cycloalkenyl, -heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus.

8. The method for the production of cyclic peptides according to claim 1, wherein the charge-stabilized leaving group is a compound of the formula

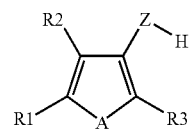

(IV)

wherein the following applies:

A is selected from O and S and

Z is selected from O and S, and whereby R1, R2, and R3 are independent of one another and are selected from:

-NO$_2$, —CN, —F, —Cl, —Br, —I, —CH$_2$Cl, —SO$_3$H, —H, —NH$_3^+$, —NL$_3^+$, —C(═O)L, —C(═O)Het, —O$^-$, —NL$_2$, —NH$_2$, —OL, —OH, —NHC(═O)L, —OC(═O)L, —SL, —CO$_2^-$, -alkyl, -alkenyl, -cycloalkyl, -cycloalkenyl, -heteroalkyl, -heterocycloalkyl, -aryl, and -heteroaryl, wherein L is selected from -alkyl, -alkenyl, -cycloalkyl, -cycloalkenyl, -heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus.

9. The method for the production of cyclic peptides according to claim 1, wherein the charge-stabilized leaving group is a compound of the formula

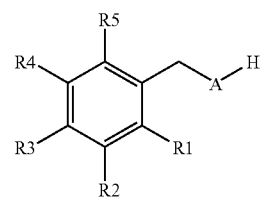

(V)

wherein the following applies:

A is selected from O and S and whereby R1, R2, R3, R4 and R5 are independent of one another and are selected from:

-NO$_2$, —CN, —F, —Cl, —Br, —I, —CH$_2$Cl, —SO$_3$H, —H, —NH$_3^+$, —NL$_3^+$, —C(═O)L, —C(═O)Het, —O$^-$, —NL$_2$, —NH$_2$, —OL, —OH, —NHC(═O)L, —OC(═O)L, —SL, —CO$_2^-$, -alkyl, -alkenyl, -cycloalkyl, -cycloalkenyl, -heteroalkyl, -heterocycloalkyl, -aryl, and -heteroaryl, wherein L is selected from -alkyl, -alkenyl, -cycloalkyl, -cycloalkenyl, -heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus.

10. The method for the production of cyclic peptides according to claim 1, wherein the peptide cyclase is a purified, isolated thioesterase domain.

11. Method for the production of a substrate and subsequent reaction of this substrate with peptide cyclases into a cyclic peptide, wherein the substrate is a linear peptide, wherein the following steps are carried out one after the other:
   adding to a free peptide acid in a solvent a reagent activating the C-terminus of the peptide acid, a coupling additive and a charge-stabilized to obtain a mixture,
   stirring the mixture at room temperature,
   adding a base to the mixture and further stirring the mixture at room temperature,
   filtering the mixture,
   removing the solvent from the mixture,
   deprotecting the linear peptide resulting from the previous steps,
   adding a peptide cyclase to the linear peptide, and
   purifying the cyclic peptide obtained,
   wherein an acyl group of the C-terminal free peptide acid of the linear peptide is bound to the charge-stabilized leaving group.

12. The method for the production of a substrate and subsequent reaction of this substrate with peptide cyclases into a cyclic peptide according to claim 11, wherein the acyl group of the C-terminal amino acid of the linear peptide is bound to one of the charge-stabilized leaving groups selected from the following:
   a.) a compound of the formula

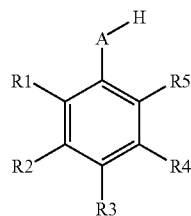

(I)

wherein the following applies:
   A is selected from O and S,
   and whereby R1, R2, R3, R4 and R5 are independent of one another and are selected from:
   -NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, and -heteroaryl, wherein L is selected from: -alkyl, -alkenyl, -cycloalkyl, -cycloalkenyl,
-heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic group stands for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus;

(b) a compound of the formula

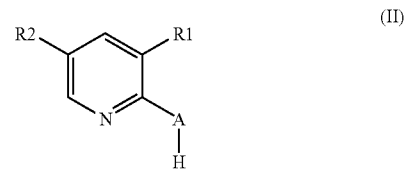

(II)

wherein the following applies:
   A is selected from O and S
   and whereby R1 and R2 are independent of one another and are selected from:
   -NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, and -heteroaryl, wherein L is selected from -alkyl, -alkenyl, -cycloalkyl, -cycloalkenyl,
-heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus;

(c) a compound of the formula

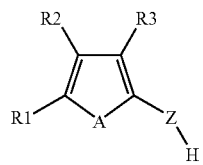

(III)

wherein the following applies:
A is selected from O and S and
Z is selected from O and S,
and whereby R1, R2, and R3 are independent of one another and are selected from:
-NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, and -heteroaryl,
wherein
L is selected from -alkyl, -alkenyl, -cycloalkyl, -cycloalkenyl,
-heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus;

(d) a compound of the formula

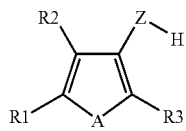

(IV)

wherein the following applies:
A is selected from O and S and
Z is selected from O and S,
and whereby R1, R2, and R3 are independent of one another and are selected from:
-NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, and -heteroaryl,
wherein
L is selected from -alkyl, -alkenyl, -cycloalkyl, -cycloalkenyl,
-heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus; and (e) a compound of the formula

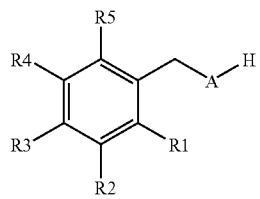

(V)

wherein the following applies:
A is selected from O and S
and whereby R1, R2, R3, R4 and R5 are independent of one another and are selected from:
-NO$_2$, —CN, —F, —Cl, —Br, —I, —CH$_2$Cl, —SO$_3$H, —H, —NH$_3^+$, —NL$_3^+$, —C(=O)L, —C(=O)Het, —O$^-$, —NL$_2$, —NH$_2$, —OL, —OH, —NHC(=O)L, —OC(=O)L, —SL, —CO$_2^-$, -alkyl, -alkenyl, -cycloalkyl, -cycloalkenyl, -heteroalkyl, -heterocycloalkyl, -aryl, and -heteroaryl,
wherein
L is selected from -alkyl, -alkenyl, -cycloalkyl, -cycloalkenyl,
-heteroalkyl, -heterocycloalkyl, -aryl, and -heteroaryl, wherein -alkyl stands for a group with 1 to 20 carbon atoms and -alkenyl for a monounsaturated or polyunsaturated group with 2 to 20 carbon atoms and -alkyl or -alkenyl are linear or branched; -cycloalkyl and -cycloalkenyl stand for a group with 3 to 20 carbon atoms; heteroalkyl stands for an alkyl group wherein up to 5 carbon atoms are substituted by atoms chosen from the group nitrogen, oxygen, sulfur, and phosphorus; the heterocyclic groups stand for a residue with 1 to 20 carbon atoms wherein up to 5 carbon atoms are substituted by heteroatoms chosen from the group nitrogen, oxygen, sulfur, and phosphorus; aryl stands for an aromatic residue with 5 to 20 carbon atoms and heteroaryl stands for a corresponding aromatic residue in which up to 5 carbon atoms are substituted by heteroatoms chosen from the group nitrogen, oxygen, sulfur, and phosphorus.

13. The method for the production of a substrate and subsequent reaction of this substrate with peptide cyclases into a cyclic peptide according to claim 12, wherein the leaving group possesses a pK$_A$ value less than or equal to 10, preferably less than or equal to 8.

14. The method for the production of a substrate and subsequent reaction of this substrate with peptide cyclases into a cyclic peptide according to claim 11, wherein DCC (dicyclohexylcarbodiimide), DCI (N,N-diisopropylcarbodiimide), PyClop (chlorotripyrrolidinophosphonium hexafluorophosphate), HBTU (2-(1H-benzotriazole-1-yl)-1,1,3,3-tetramethyluronium hexafluorophosphate), HATU (2-(7-aza-1H-benzotriazole-1-yl)-1,1,3,3,-tetramethyluronium hexafluorophosphate), HOSu (N-hydroxysuccinimide), TBTU (2-(1H-benzotriazole-1-yl)-1,1,3,3-tetramethylaminium tetrafluoroborate), T3P (propylphosphonic anhydride), BopCl (bis(2-oxo-3-oxazolidinyl)phosphonic chloride) or 3-C1-1-pyridinium iodide is used as the reagent for activating the free C-terminus or a side chain carboxylic acid of the peptide carboxylic acid.

15. The method for the production of a substrate and subsequent reaction of this substrate with peptide cyclases into a cyclic peptide according to claim 11, wherein HOBt (N-hydroxybenzotriazole), HOAt (1-hydroxy-7-azabenzotriazole) or HONB (N-hydroxy-5-norbornene -2,3-dicarboxylimide) is used as the coupling additive.

\* \* \* \* \*